United States Patent [19]

Krishnamurti et al.

[11] Patent Number: 5,914,408
[45] Date of Patent: Jun. 22, 1999

[54] OLEFIN POLYMERIZATION CATALYSTS CONTAINING BENZOTHIAZOLE

[75] Inventors: Ramesh Krishnamurti, Williamsville; Sandor Nagy, Grand Island; John Tyrell, Williamsville, all of N.Y.; Bradley P. Etherton, Houston, Tex.

[73] Assignee: Equistar Chemicals, LP, Houston, Tex.

[21] Appl. No.: 09/130,846

[22] Filed: Aug. 7, 1998

[51] Int. Cl.$^6$ .............. C07F 17/00; C07F 7/00; C08F 110/02; B01J 31/00
[52] U.S. Cl. .............. 548/105; 502/103; 502/117; 502/155; 526/134; 526/160; 526/205; 526/352; 556/7; 556/53; 556/1; 556/144; 556/148; 556/43; 556/58; 548/108; 548/165
[58] Field of Search .............. 548/105, 108, 548/165; 556/7, 53, 1, 144, 146, 43, 58; 502/103, 117, 155; 526/134, 160, 205, 352

[56] References Cited

U.S. PATENT DOCUMENTS

| | | | |
|---|---|---|---|
| 2,870,157 | 1/1959 | Csendes | 260/299 |
| 3,043,847 | 7/1962 | Wilde | 260/299 |
| 3,114,633 | 12/1963 | Schlesinger | 96/1 |
| 5,539,124 | 7/1996 | Etherton et al. | 548/402 |
| 5,554,775 | 9/1996 | Krishnamurti et al. | 556/7 |

*Primary Examiner*—Porfirio Nazario-Gonzalez
*Attorney, Agent, or Firm*—Locke Liddell & Sapp, LLP

[57] ABSTRACT

A novel metallocene catalyst for the polymerization of olefin (co)polymers is of the general formula:

$$\text{Benzothiazole}-\text{E}-\text{M}-\text{X}_m\text{L}_n$$

where,

M is a transition metal of Groups 3–10 of the Periodic Table;

E is sulfur or oxygen; E being bond to the transition metal and to the carbon atom between sulfur and nitrogen of the benzothiazole moiety;

L is a polymerization-stable anionic ancillary ligand;

X is a halogen, alkoxy from $C_1$ to $C_{20}$, siloxy from $C_1$ to $C_{20}$, $N(R_1)_2$, a hydrocarbyl group containing up to about 12 carbon atoms or hydrogen or mixtures thereof; preferably X is halogen, methoxy, ethoxy or siloxy $(R_1)_3SiO$—, where $R_1$ is alkyl from $C_1$ to $C_{20}$; and m+n equals the valency of the M minus 1.

20 Claims, No Drawings

OLEFIN POLYMERIZATION CATALYSTS CONTAINING BENZOTHIAZOLE

FIELD OF THE INVENTION

This invention relates to a novel metallocene catalyst system containing a catalyst wherein one of the two polymerization-stable anionic ancillary ligands of the catalyst is a benzothiazolyl group. The invention farther relates to a method of preparation of the catalyst and a method of using the same.

BACKGROUND OF THE INVENTION

Historically, polyolefins have been made with conventional Ziegler catalyst systems. Such catalysts typically consist of transition metal-containing compounds and one or more organometallic compounds. For example, polyethylene has been made using such Ziegler catalysts as titanium trichloride and diethylaluminum chloride, as well as a mixture of titanium tetrachloride, vanadium oxytrichloride, and triethylaluminum.

While these catalysts are inexpensive, they exhibit low activity and therefore must be used at high concentrations. As a result, it is sometimes necessary to remove catalyst residues from the polymer, which adds to production costs. Neutralizing agents and stabilizers must be added to the polymer to overcome the deleterious effects of the catalyst residues. Failure to remove catalyst residues leads to polymers having a yellow or grey color and poor ultraviolet and long term stability. Additionally, for example, chloride-containing residues can cause corrosion in polymer processing equipment.

Furthermore, Ziegler catalysts produce polymers having a broad molecular weight distribution which is undesirable for some applications such as injection molding. They are also poor at incorporating α-olefin co-monomers. Poor co-monomer incorporation makes it difficult to control the polymer density. Large quantities of excess co-monomer may be required to achieve a certain density and many higher α-olefins, such as 1-octene, may be incorporated at only very low levels, if at all.

Although significant improvements in Ziegler catalyst systems have occurred since their initial discovery, they lately have been substantially replaced with "single-site," in particular, metallocene, catalyst systems. A traditional metallocene catalyst typically consists of a transition metal compound which has one or more cyclopentadienyl ring ligands bound in an $\eta^5$ fashion. The cyclopentadienyl ring ligands are polymerization-stable; that is, they remain bound to the metal during the course of the polymerization process. They produce polymers of high molecular weight and display narrow molecular weight distributions, because the cyclopentadienyl ligands deter formation of secondary polymerizing species. These catalysts also incorporate α-olefin co-monomers well. However, at higher temperatures traditional metallocene catalysts tend to produce lower molecular weight polymers. They are particularly useful for gas phase and slurry polymerizations of ethylene, which are conducted at about 80° C. to about 95° C., but are less useful in solution polymerizations of ethylene, at about 150° C. to about 250° C. Additionally, gas phase and slurry polymerizations using supported metallocene catalysts can suffer from sheeting and equipment fouling problems.

Recently, catalysts have been discovered wherein one or more of the cyclopentadienyl ring ligands associated with the traditional metallocene have been replaced by other polymerization-stable anionic ancillary ligands. These may be ligands which are isolobal to cyclopentadienyl; that is, the frontier molecular orbitals—the highest occupied and lowest unoccupied molecular orbitals—of the ligand and those of the cyclopentadienyl ligand are similar. These isolobal ligands may include tris(pyrazolyl)borates, pentadienyl groups, phospholes, and carbollides.

In particular, U.S. Pat. No. 5,554,775, incorporated herein by reference, discloses catalysts wherein one or both cyclopentadienyl moieties are replaced by a borabenzene moiety including boranaphthalene and boraphenanthrene. Further, U.S. Pat. No. 5,539,124, incorporated herein by reference, discloses catalysts in which one or both cyclopentadienyl moieties have been replaced by a nitrogen-containing heteroaromatic compound containing a pyrrolyl ring, i.e., an azametallocene, variously substituted. The heteroaromatics disclosed in the latter patent include, e.g., indolyl, isoindolyl, and carbazolyl, and other homologous heteroaromatic moieties. The foregoing heteroaromatic catalysts may be referred to generally as heterometallocenes. In addition, PCT International Application WO 96/34021 discloses azaborolinyl heterometallocenes wherein at least one aromatic ring is complexed with a transition metal. Such rings include both a boron atom and a nitrogen atom. These specifically will be referred to as, e.g., azaborolines and the catalysts derived therefrom as azaborolinyl catalysts. The latter catalysts also fall into the general group referred to as heterometallocenes. The foregoing metallocene and heterometallocene catalysts have been developed to include bulky ligands attached to the aromatic moieties. Increased control of the polymerization process may therefore be provided.

Because supported catalysts are more stable, may produce higher molecular weight polymers, and may produce useful changes in the morphology of the polymer, metallocene catalysts are often used in conjunction with a support, such as silica gel.

For the purposes of the present disclosure, it is to be understood that when the term "metallocene" is used, both traditional metallocenes and heterometallocenes such as those disclosed in the above referenced U.S. patents and applications, including those containing bulky ligands, are contemplated to fall within the scope of the term. Thus, "metallocene" is considered to be a generic term for all such transition metal-bonded aromatic organic polymerization catalysts. Likewise, it is to be understood that when the term "single-site" catalyst is used, both metallocenes as well as other metal complexes containing polymerization-stable ancillary ligands are contemplated to fall within the scope of the term.

SUMMARY OF THE INVENTION

The invention relates to a novel catalyst system containing at least one polymerization-stable anionic ancillary ligand derived from a benzothiazolyl group and a Group 3–10 metal. The benzothiazolyl group is attached to the metal, M, via an electron rich element such as oxygen or sulfur. The benzothiazolyl group presumably stabilizes the active metal center to achieve high productivity, good comonomer incorporation, and narrow molecular weight distribution characteristic of the single site catalyst.

DESCRIPTION OF THE PREFERRED EMBODIMENTS

A novel metallocene catalyst for the polymerization of olefin homopolymers and co-polymers is of the general formula:

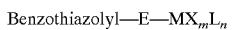

Benzothiazolyl—E—MX$_m$L$_n$ where
  M is a transition metal of Groups 3–10, preferably Groups 3–7, more preferably Groups 4–6, and most preferably Groups 4–5, of the Periodic Table;
  E is bonded to M and to the carbon atom (between sulfur and nitrogen of the benzothiazole moiety) and is either sulfur or oxygen;
  Benzothiazolyl is represented by the formula:

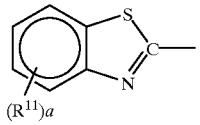

(I)

where
  a is 0 to 4;
  $R^{11}$ is a halogen, $C_1$–$C_8$ alkyl, $C_6$–$C_{24}$ aryl, $C_6$–$C_{24}$ alkaryl or aralkyl group, alkoxy of 1 to 12 carbon atoms or silyl group of the formula —Si(R)$_3$ where R is a $C_1$–$C_6$ alkyl group;
  if on vicinal carbon atoms on the ring, two alkyl or aryl $R^{11}$ groups may be connected to form a ring fused to the benzothiazolyl ring;
  L is a polymerization-stable anionic ancillary ligand;
  X is a halogen (preferably —Cl or —Br), alkoxy from $C_1$ to $C_{20}$, siloxy from $C_1$ to $C_{20}$, dialkylamido, (N(R$_1$)$_2$), a hydrocarbyl group containing up to about 12 carbon atoms, hydrogen or another univalent anionic ligand, or mixtures thereof; preferably X is chloride, methyl, benzyl, methoxy, ethoxy, dimethylamido or siloxy (R$_1$)$_3$SiO—, where R$_1$ is alkyl from $C_1$ to $C_{20}$, preferably $C_1$ to $C_6$; and
  m+n equals the valency of the M minus 1
wherein,
  L and the benzothiazolyl group may be bridged.
  The transition metal, M, may be any Group 3 to 10 metal or a metal from the lanthanide or actinide series. In a preferred embodiment, the catalyst contains a Group 4, 5, or 6 transition metal. In a particularly preferred embodiment, the catalyst contains a Group 4 metal, particularly zirconium, titanium or hafnium.
  L may be cyclopentadienyl, boraaryl, pyrrolyl, azaborolinyl, pyridinyl, quinolinyl or homologous ligands. Typical L in the catalyst of the invention are the mono- or bi-cyclopentadienyl or substituted cyclopentadienyl radicals, especially those of the formulae:

$(C_5R^1{}_w)_fR^2{}_s(C_5R^1{}_w)$  (II)

and $R^2{}_s(C_5R^1{}_w)_2$  (III)

wherein,
  ($C_5R^1{}_w$) is a cyclopentadienyl or substituted cyclopentadienyl; each $R^1$ is the same or different and is hydrogen or a hydrocarbyl radical such as alkyl, alkenyl, aryl, alkaryl or aralkyl radical containing from 1 to 20 carbon atoms of which two carbon atoms may be joined together to form a $C_4$–$C_6$ ring;
  $R^2$ is a $C_1$–$C_{20}$ alkylene radical, a dialkyl germanium or silicon [such as silyl or a radical of the formula —Si(R$_5$)$_2$ wherein each R$_5$ is H, a $C_1$–$C_{10}$ (preferably a $C_1$–$C_4$) alkyl group, an aryl such as benzyl or phenyl or a benzyl or phenyl group substituted with one or more $C_1$–$C_4$ alkyl groups] or an alkyl phosphine or amine radical bridging two ($C_5R^1{}_w$) rings;
  s is 0 or 1;
  f is 0, 1 or 2 provided that when f is 0, s is 0;
  w is 4, when s is 1; and
  w is 5, when s is 0.
  Particularly good results are obtained where the cyclopentadienyl ring is of the structure:

(IV)

where each substituent group, $R_2$, is independently selected from a $C_1$ to $C_{20}$ hydrocarbyl group and r is a number from 0 to 5. In the case in which two $R_2$ groups are vicinal, they can be joined to produce a ring which is fused to the cyclopentadienyl ring. Examples of alkyl substituted cyclopentadienyl rings include n-butylcyclopentadienyl, methyl-cyclopentadienyl and pentamethylcyclopentadienyl. Examples of fused cyclopentadienyl ring ligands include indenyl, tetrahydroindenyl, fluorenyl and 2-methylindenyl.

The ligand L for use in the olefin polymerization catalyst for the invention may further contain 4 to 30 carbon atoms and may contain a fused ring, one of which is a pyrrolyl ring. Included within this group are heterocyclic radicals of the formula:

(V)

wherein,
  R' is independently hydrogen or $R^{80}$ or with F forms a $C_4$ to $C_{10}$ fused ring;
  each $R^{80}$ is independently selected from hydrogen, a $C_1$ to $C_{20}$, preferably a $C_1$ to $C_6$, aliphatic or cycloaliphatic radical; a $C_6$–$C_{30}$, preferably a $C_6$–$C_{15}$, aryl radical, or a $C_7$–$C_{30}$, preferably a $C_7$–$C_{15}$, aralkyl or alkaryl radical;
  W independently represents a trivalent atom selected from nitrogen, phosphorus, arsenic, antimony and bismuth; and
  F is independently selected from carbon and W.

Exemplary compounds include those wherein R' is —H or a $C_1$ to $C_6$ alkyl group or $C_6$ to $C_{10}$ aryl group. Preferred compounds include 2-methylpyrrolyl, 3-methylpyrrolyl, 2,5-dimethylpyrrolyl, 2,5-di-tert-butylpyrrolyl, aryl substituted pyrrolyl rings such as 2-phenylpyrrolyl, 2,5-diphenylpyrrolyl, indolyl and alkyl substituted indolyls of the formula:

(VI)

such as 2-methylindolyl, 2-tert-butylindolyl, 3-n-butylindolyl, 7-methylindolyl, and 4,7-dimethylindolyl and carbazolyl and alkyl substituted carbazolyls of the formula:

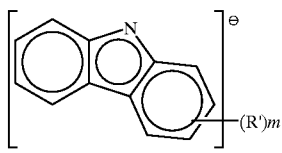
(VII)

where m=0 to 7 and R' is as defined above. The alkyl and aryl substituents on the pyrrolyl ring-containing ligand are not on the nitrogen atom in the ring but are on the carbon atoms of the ring.

Additional examples of ring structures include:

1-Phospha-2,3,4,5-tetramethylcyclopentadienyl,
1-Phospha-3,4-diphenylcyclopentadienyl,
1-Phosphaindenyl)zirconium trichloride,
1-Phospha-3-methoxycyclopentadienyl,
1,3-Diphospha-4,5-diphenylcyclopentadienyl,
1,2,4-Triphospha-3,5-diphenylcyclopentadienyl,
1,2,3,4-Tetraphospha-5-phenylcyclopentadienyl,
Pentaphosphacyclopentadienyl,
Imidazolyl,
Pyrazolyl,
1,2,3-triazolyl,
1,2,4-triazolyl,
Tetrazolyl, and
Pentazolyl.

Still further, the ligand L may be of the formula:

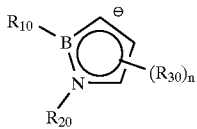
(VIII)

wherein $R_{10}$ is independently selected from $R_{25}$, alkaryl from $C_6$ to $C_{12}$, aralkyl from $C_6$ to $C_{12}$, hydrogen, or $Si(R_{25})_3$, $R_{25}$ is alkyl from $C_1$ to $C_{12}$, or aryl from $C_6$ to $C_{12}$, $R_{20}$ is $R_{10}$, halogen, or $COR_{25}$, $R_{30}$ is $R_{20}$, $OR_{25}$, $N(R_{25})_2$, $SR_{25}$, or a fused ring system and n is 0 to 3.

The $R_{25}$ group is preferably alkyl from $C_1$ to $C_4$, the $R_{10}$ group is preferably $C_1$ to $C_6$ alkyl or —$Si(R_{25})_3$ and the $R_{30}$ group is preferably hydrogen or methyl. Examples of fused ring structures that can be used include:

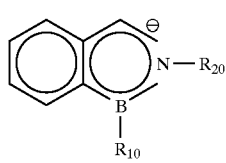
(IX)

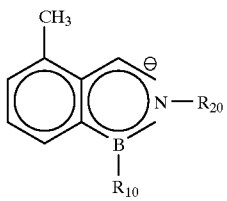
(X)

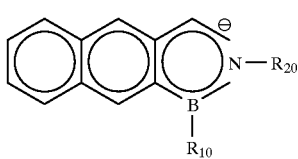
(XI)

The L ligand may further be a boratabenzene ligand. A boratabenzene ring has the structure:

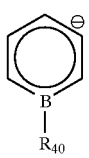
(XII)

where $R_{40}$ can be hydrogen $N(R_{50})_2$, $OR_{50}$, or $R_{50}$, where each $R_{50}$ is independently selected from alkyl from $C_1$ to $C_{10}$, aryl from $C_6$ to $C_{15}$, alkaryl from $C_7$ to $C_{15}$, and aralkyl from $C_7$ to $C_{15}$. The $R_{40}$ group is preferably —$N(R_{50})_2$, methyl or phenyl and, if $R_{40}$ is —$N(R_{50})_2$, then the $R_{50}$ in —$N(R_{50})_2$ is preferably methyl.

Exemplary of the boratabenzene ligands include:

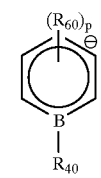
(XIII)

(boratabenzene)

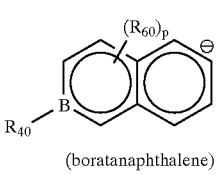
(XIV)

(boratanaphthalene)

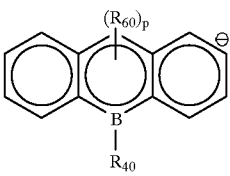
(XV)

(boratanthracene)

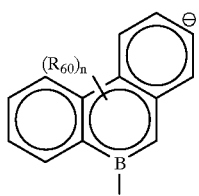

(borataphenanthrene)

where "p" is 0 to the maximum number of substitutable positions, and is preferably 0 or 1. Each $R_{60}$ is independently selected from halogen, alkoxy from $C_1$ to $C_{10}$, silyl (—Si$(R_{50})_3$) and $R_{50}$. Particularly preferred boratabenzene ligands are 1-methyl-1 boratabenzene, 2-phenyl-2 boratanaphthalene and 9-mesityl-9 borataanthracene and 1-methyl-2-trimethylsilyl-1-boratabenzene.

Still, L may be selected from the radicals:

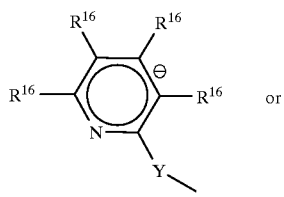

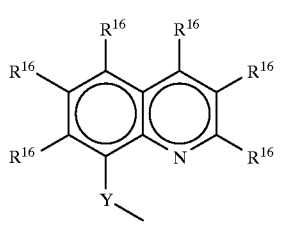

wherein $R^{16}$ is independently selected from $R^{85}$, $C_1$ to $C_6$ alkoxy, $C_7$ to $C_{20}$ alkaryl, $C_7$ to $C_{20}$ aralkyl, halogen, or $CF_3$; each $R^{85}$ is independently selected from hydrogen, $C_1$ to $C_6$ alkyl, or $C_6$ to $C_{14}$ aryl and Y is O, S, $NR^{85}$, $PR^{85}$.

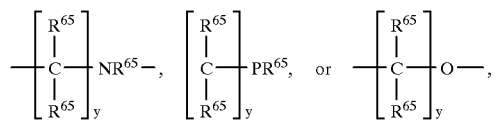

where $R^{65}$ is a $C_1$ to $C_6$ alkyl and y is 1 to 4.

Groups that can be used to bridge two ligands include methylene, ethylene, 1,2-phenylene, dimethylsilyl, diphenylsilyl, diethylsilyl, and methyl phenyl silyl. Normally, only a single bridge is used in a catalyst. It is believed that bridging the ligand changes the geometry around the catalytically active transition metal and improves catalyst activity and other properties, such as comonomer incorporation and thermal stability.

The catalysts of this invention can be prepared by reacting the mercaptobenzothiazole or the hydroxybenzothiazole with a strong base such as n-butyl lithium. This results in the desired benzothiazole anion. Stoichiometric quantities of these reactants are used typically used. The reaction is preferably performed by dissolving the reactants in an organic solvent which does not have an active proton such as tetrahydrofuran, anisole, or ethyl ether. The solution should be as concentrated as possible to reduce the amount of solvent that must be handled.

The reaction mixture is then added to a slurry of the transition metal complex with L in an organic solvent as described above. For example, lithium (2-sulfidyl-benzothiazole) could be added to (1-tert-butyl-2-methylazaborolinyl) zirconium trichloride in ether. This would produce (benzothiazole-2-sulfidyl) (1-tert-butyl-2-methylazaborolinyl) zirconium dichloride and lithium chloride. The reaction can occur at room temperature, but low temperature is preferred to reduce the amount of undesirable by-products. Stoichiometric quantities are typically used. The by-products are removed by filtration, the solvent is evaporated, and the catalyst is collected.

The catalysts of the invention have a narrow molecular weight distribution and typically exhibit a ratio of $MI_{20}$ vs. $MI_2$ between about 10 to about 25. The catalysts of the invention may be single site catalysts.

Since the catalyst of the invention is normally used in conjunction with a co-catalyst, it is preferable to dissolve the transition metal complex in a solvent in which the co-catalyst is also soluble. For example, if methylalumoxane (MAO) is the co-catalyst, then toluene, xylene, benzene, or ethyl benzene could be used as the solvent.

Representative co-catalysts for use in the invention include alumoxanes, optionally with aluminum alkyls of the formula $Al(R^7)_3$ where $R^7$ independently denotes a $C_1$–$C_8$ alkyl group, hydrogen or halogen. Exemplary of the latter of such co-catalysts are triethylaluminum, trimethylaluminum and tri-isobutylaluminum. The alumoxanes are polymeric aluminum compounds typically represented by the cyclic formulae $(R^8—Al—O)_s$ and the linear formula $R^8(R^8—Al—O)_sAlR^8$ wherein $R^8$ is a $C_1$–$C_5$ alkyl group such as methyl, ethyl, propyl, butyl and pentyl and s is an integer from 1 to about 20. Preferably, $R^8$ is methyl and s is about 4 to about 10. Representative but non-exhaustive examples of alumoxane co-catalysts are (poly)methylalumoxane (MAO), ethylalumoxane and diisobutylalumoxane.

Examples of suitable co-catalysts include MAO and mixtures of MAO with other aluminum alkyls such as triethylaluminum, trimethylaluminum, tri-isobutylaluminum, ethylalumoxane, or diisobutyl alumoxane. The preferred co-catalyst is MAO as it results in high catalyst activity, good comonomer incorporation, and a polymer having a narrower molecular weight distribution.

The co-catalyst can further be a substituted or unsubstituted tri-alkyl or tri-aryl boron derivative, such as tris (perfluorophenyl)boron as well as ionic compounds such as tri (n-butyl)ammonium tetrakis (pentafluorophenyl) boron or trityl tetrakis(perfluorophenyl)boron which ionize the neutral metallocene compound. Such ionizing compounds may contain either an active proton, or a cation associated with, but not coordinated or only loosely coordinated to, the remaining ion of the ionizing compound. See, for instance, U.S. Pat. Nos. 5,153,157; 5,198,401; and 5,241,025, all of which are herein incorporated by reference.

It is preferable not to premix the catalyst and the co-catalyst as this may result in lower catalyst activity. Rather, the catalyst and co-catalyst are preferably injected separately into a reactor containing the monomer to be polymerized. And, preferably, the co-catalyst is injected first. The amount of cocatalyst used with the transition metal compound can be in a molar ratio ranging from about 1:1 to about 15,000:1.

The catalyst and co-catalyst can also be used on a support such as silica gel, alumina, magnesia, or titania. Supports are not generally preferred as they leave additional contaminants in the polymer. However, a support may be required depending upon the process being utilized. For example, a support is generally needed in gas phase polymerization processes and slurry polymerization processes in order to control the particle size of the polymer being produced and in order to prevent fouling of the reactor walls. In order to use a support, the catalyst is dissolved in a solvent and is deposited onto the support material by evaporating the solvent. The cocatalyst can also be deposited on the support or it can be introduced into the reactor separately from the supported catalyst.

Once the catalyst has been prepared it should be used as promptly as possible as it may lose some activity during storage. Storage of the catalyst should be at a low temperature, such as −100° C. to 20° C. The catalyst is used in a conventional manner in the polymerization of unsaturated olefinic monomers.

The catalyst is also useful for copolymerizing mixtures of ethylene with unsaturated monomers such as 1-butene, 1-hexene, 1-octene, and the like; mixtures of ethylene and di-olefins such as 1,3-butadiene, 1,4-hexadiene, 1,5-hexadiene, and the like; and mixtures of ethylene and unsaturated comonomers such as norbornadiene, ethylidene norbornene, vinyl norbornene, and the like.

While unsaturated monomers such as styrene can be polymerized using the catalysts of this invention, it is particularly useful for polymerizing α-olefins such as propylene, 1-butene, 1-hexene, 1-octene, and especially ethylene.

The catalysts of this invention can be utilized in a variety of different polymerization processes. They can be utilized in a liquid phase polymerization process (slurry, solution, suspension, bulk phase, or a combination of these), in a high pressure fluid phase, or in a gas phase polymerization process. The processes can be used in series or as individual single processes. The pressure in the polymerization reaction zones can range from about 15 psia to about 50,000 psia and the temperature can range from about −100° C. to about 300° C.

EXAMPLES

Example 1

This example describes the synthesis of benzothiazole-2-sulfidyl cyclopentadienyl zirconium dichloride of the structural formula:

(XIX)

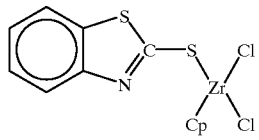

To 0.836 gram (0.005 mole) 2-mercaptobenzothiazole dissolved in 30 ml. of dry tetrahydrofuran under an argon atmosphere and cooled in a dry ice bath was added 3.1 ml of 1.6M n-butyl lithium in hexane (0.005 mole). After stirring for 20 minutes, this mixture was added via cannula to a stirring slurry of 1.31 grams (0.005 mole) cyclopentadienylzirconium trichloride and 30 ml of dry tetrahydrofuran that had been cooled with a dry ice bath. After 30 minutes, the dry ice bath was removed and the reaction mixture stirred an additional 30 minutes as the mixture warmed to room temperature. The volatiles were removed with vacuum and the resultant solid dissolved in dry toluene. After stirring for 30 minutes to complete dissolution, the solution was filtered and vacuum was applied to remove volatiles. A green solid was produced.

Examples 2–6

These examples are directed to the polymerization of ethylene in the presence of the catalyst of the invention. In these five examples, ethylene was polymerized using the catalyst of Example 1. The polymerization was conducted in a stirred 1.7 liter stainless steel autoclave at 80° C. and 110° C. Dry, oxygen-free toluene (840 ml) was charged to the dry oxygen-free reactor. 10% MAO in toluene (from Ethyl Corporation) is typically added with syringe without further purification. The reactor was then heated to the desired temperature and sufficient ethylene was added to bring the reactor pressure to 150 psig. The reactor was allowed to equilibrate at the desired temperature and pressure. A solution of catalyst was prepared by dissolving 0.100 grams of product in 100 ml of toluene and the desired amount was added to the reactor.

At the end of one hour the ethylene flow was stopped and the reactor was rapidly cooled to room temperature. The polymer was filtered from the toluene, dried in a vacuum oven and weighed. In the following, Exhibit 1 lists polymerization conditions and Exhibit 2 the results of polymerizations.

The melt index of the polymer was measured according to ASTM D-1238, Condition E and Condition F. MI is the melt index measured with a 2.16 Kg weight (Condition E). HLMI is the melt index measured with a 21.6 kg weight (Condition F). The melt flow ratio (MFR) is defined as the ratio of HLMI (or MI$_{20}$) of MI(or MI$_2$) and is a measure of molecular weight distribution. A MFR below 25 indicates narrow molecular weight distribution and is likely to demonstrate improved properties charactersitc of a single site catalyst (or an metallocene). Typically a Ziegler-Natta catalyst yields polymer with a MFR of around 35.

Exhibit 1. Polymerization Conditions

| Example | Reactor Temp. (C.) | Time, Min | Hydrogen Delta P, psi (mmoles) | Comonomer | Catalyst (mmoles) | Co-Catalyst | Al/M (atomic) |
|---|---|---|---|---|---|---|---|
| 2 | 80 | 60 | 0 | None | 0.0057 | MAO | 1579 |
| 3 | 80 | 60 | 0 | None | 0.0043 | MAO | 2103 |
| 4 | 110 | 60 | 0 | None | 0.0057 | MAO | 1579 |
| 5 | 110 | 60 | 30 | None | 0.0057 | MAO | 1579 |
| 6 | 110 | 60 | 30 | Butene, 20 ml | 0.0057 | MAO | 1580 |

Exhibit 2. Polymerization Results

| Example | Wt. PE (g) | Catalyst Acitvity kg/g/hr (kg/g Zr/hr) | MI dg/min | HLMI dg/min | MFR | Density g/ml |
|---|---|---|---|---|---|---|
| 2 | 50.2 | 96.5 | 0.0246 | 0.2851 | 11.59 | — |
| 3 | 47.0 | 120.0 | 0.034 | 0.2921 | 8.59 | — |
| 4 | 42.4 | 81.6 | 0.182 | 3.41 | 18.74 | 0.9637 |
| 5 | 44.9 | 86.4 | 1.62 | 39.6 | 24.44 | 0.9690 |
| 6 | 45.2 | 86.9 | 4.86 | 98.7 | 20.30 | 0.9504 |

In example 6, the comonomer incorporation is indicated by the effective density depression.

What is claimed is:

1. A catalyst of the general formula:

$$\text{Benzothiazole—E—MX}_m\text{L}_n$$

where,

M is a transition metal of Groups 3–10 of the Periodic Table;

E is sulfur or oxygen; E being bonded to the transition metal and to the carbon atom between sulfur and nitrogen of the benzothiazole moiety;

L is a polymerization-stable anionic ancillary ligand;

X is a halogen, alkoxy from $C_1$ to $C_{20}$, siloxy $(R_1)_3SiO$— from $C_1$ to $C_{20}$, dialkylamido, $(N(R_1)_2)$, a hydrocarbyl group containing up to about 12 carbon atoms or hydrogen or mixtures thereof; where $R_1$ is alkyl from $C_1$ to $C_{20}$; and m+n equals the valency of the M minus 1.

2. The catalyst of claim 1, wherein L is a substituted or unsubstituted cyclopentadienyl, boraaryl, pyrrolyl, azaborolinyl, quinolinyl or pyridinyl group.

3. The catalyst of claim 1, wherein M is a metal of Groups 3 to 7.

4. The catalyst of claim 3, wherein M is a metal of Groups 4 to 6.

5. The catalyst of claim 4, wherein M is a Group 4 metal.

6. The catalyst of claim 5, wherein M is titanium or zirconium.

7. The catalyst of claim 6, wherein X is chlorine or bromine.

8. The catalyst of claim 1, wherein X is chlorine or bromine.

9. The catalyst of claim 1 having the structure:

10. The catalyst of claim 1 having the structure:

wherein BB is a boroaryl group.

11. The catalyst of claim 1, having the structure wherein Az is an azaborolinyl group.

12. A catalyst system comprising the catalyst of claim 1 and a cocatalyst.

13. The catalyst system of claim 12, wherein the cocatalyst is an aluminoxane.

14. The catalyst of claim 12, wherein the cocatalyst is a trialkyl or triaryl boron derivative.

15. The catalyst system of claim 12, wherein the cocatalyst is a neutral boron containing compound or anionic borate.

16. The catalyst system of claim 12, wherein the catalyst is a supported catalyst.

17. A method of polymerizing an unsaturated olefinic monomer comprising contacting said monomer with the catalyst according to claim 1.

18. The method of claim 17, wherein the olefinic monomer is ethylene or is ethylene and a second alpha-olefin.

19. A method of polymerizing an unsaturated olefinic monomer comprising contacting said monomer with the catalyst system of claim 12.

20. The method of claim 19, wherein the olefinic monomer is ethylene or is ethylene and a second alpha-olefin.

* * * * *